United States Patent [19]

Phaff

[11] Patent Number: 5,162,544

[45] Date of Patent: Nov. 10, 1992

[54] INDOLINE-CONTAINING PHTHALIDES

[75] Inventor: Rox Phaff, Itingen, Switzerland

[73] Assignee: Ciba-Geigy Corporation, Ardsley, N.Y.

[21] Appl. No.: 638,875

[22] Filed: Jan. 8, 1991

[30] Foreign Application Priority Data

Jan. 11, 1990 [CH] Switzerland ............... 00084/90

[51] Int. Cl.$^5$ .......................... C07D 405/06
[52] U.S. Cl. ........................ 548/463; 548/427
[58] Field of Search ............ 548/463, 427, 450, 451

[56] References Cited

U.S. PATENT DOCUMENTS

| 4,119,776 | 10/1978 | Farber | 548/463 |
| 4,876,357 | 10/1989 | Phaff | 548/463 |
| 5,004,813 | 4/1991 | Phaff | 548/463 |

FOREIGN PATENT DOCUMENTS 0242169 10/1987 European Pat. Off.
0266310  5/1988 European Pat. Off.

OTHER PUBLICATIONS

Chem. Abstrt. 98: 71864u, 1983.

Primary Examiner—Robert W. Ramsuer
Assistant Examiner—Jacqueline Haley
Attorney, Agent, or Firm—Marla J. Mathias; Edward M. Roberts

[57] ABSTRACT

Pyrroline- or indoline-containing phthalides of formula

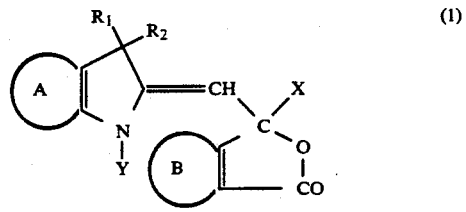

wherein
  $R_1$ and $R_2$ are each independently of the other lower alkyl, $C_5$–$C_7$cycloalkyl or benzyl or, when taken together, are $C_4$–$C_6$alkylene,
  Y is alkyl or not more than 12 carbon atoms, unsubstituted or substituted by halogen, cyano, hydroxy or lower alkoxy, or is benzyl,
  X is hydrogen, alkyl of 1 to 12 carbon atoms or an aryl radical, and the ring A is a benzene or naphthalene ring which is unsubstituted or substituted by one or more members selected from the group consisting of halogen, cyano, lower alkyl, lower alkoxy or lower alkoxycarbonyl, and the ring B is an aromatic or heteroaromatic radical which contains 6 ring atoms and which may contain an aromatic fused ring, which ring B as well as the fused ring may be substituted.

These phthalides are particularly suitable for use as color formers in pressure- or heat-sensitive recording materials and give lightfast yellow, orange or red images.

9 Claims, No Drawings

INDOLINE-CONTAINING PHTHALIDES

The present invention relates to pyrroline- or indoline-containing phthalides, to their preparation and to the use thereof as colour formers in pressure-sensitive or heat-sensitive recording materials.

The phthalides of this invention have the general formula

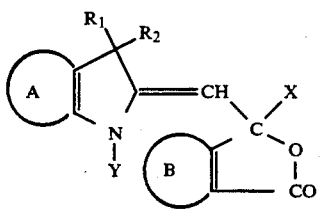

(1)

wherein
$R_1$ and $R_2$ are each independently of the other lower alkyl, $C_5$–$C_7$cycloalkyl or benzyl or, when taken together, are $C_4$–$C_6$alkylene, Y is alkyl of not more than 12 carbon atoms, unsubstituted or substituted by halogen, cyano, hydroxy or lower alkoxy, or is benzyl, X is hydrogen, alkyl of 1 to 12 carbon atoms or an aryl radical, and the ring A is a benzene or naphthalene ring which is unsubstituted or substituted by one or more members selected from the group consisting of halogen, cyano, lower alkyl, lower alkoxy or lower alkoxycarbonyl, and the ring B is an aromatic or heteroaromatic radical which contains 6 ring atoms and which may contain an aromatic fused ring, which ring B as well as the fused ring may be substituted.

The ring A is preferably an unsubstituted benzene ring or a benzene ring which is substituted by halogen, cyano or lower alkyl. The ring A is most preferably an unsubstituted or a halogen-substituted benzene ring.

A 6-membered aromatic ring B is preferably a benzene ring which is unsubstituted or substituted by halogen, cyano, nitro, lower alkyl, lower alkoxy, lower alkylthio, lower alkylcarbonyl, lower alkoxycarbonyl, amino, lower alkylamino, di-lower alkylamino or lower alkylcarbonylamino. A 6-membered heterocyclic ring B is preferably a nitrogen-containing heterocycle having aromaticity, for example a pyridine or pyrazine ring. The ring B may also contain a fused aromatic ring, preferably a benzene ring, and is therefore typically a naphthalene, quinoline or quinoxaline ring.

Preferred 6-membered aromatic or heterocyclic radicals B are the 2,3-pyridino, 3,4-pyridino, 2,3-pyrazino, 2,3-quinoxalino, 1,2-naphthalino, 2,3-naphthalino or 1,2-benzo radical, each unsubstituted or substituted by halogen such as chloro or bromo, nitro, lower alkyl, lower alkoxy, lower alkylthio or an unsubstituted or substituted amino group as defined above. The unsubstituted 1,2-benzo radical or the 1,2-benzo radical which is substituted by chloro, lower alkoxy or di-lower alkylamino, preferably dimethylamino, is especially preferred.

The substituents $R_1$ and $R_2$ may be different from each other or are preferably identical. $R_1$ and $R_2$ are preferably lower alkyl and, most preferably, are both methyl. $R_1$ together with $R_2$ as alkylene preferably contain 4 or 5 carbon atoms and, together with the linking carbon atom, can form a cyclopentane, cycloheptane or, preferably, cyclohexane ring.

$R_1$ and $R_2$ as cycloalkyl typically represent cycloheptyl, cycloheptyl or, preferably, cyclohexyl.

The N-substituent Y as alkyl may be straight-chain or branched alkyl and typically represents methyl, ethyl, n-propyl, isopropyl, n-butyl, 1-methylbutyl, tert-butyl, sec-butyl, amyl, isopentyl, n-hexyl, 2-ethylhexyl, isooctyl, n-octyl, 1,1,3,3-tetramethylbutyl, nonyl, isononyl, 3-ethylheptyl, decyl or n-dodecyl.

A substituted alkyl radical Y is preferably cyanoalkyl, haloalkyl, hydroxyalkyl or alkoxyalkyl, each preferably containing a total of 2 to 8 carbon atoms. Exemplary of such radicals are 2-cyanoethyl, 2-chlorethyl, 2-hydroxyethyl, 2-methoxyethyl, 2-ethoxyethyl, 2,3-dihydroxypropyl, 2-hydroxy-3-cholopropyl, 3-methoxypropyl, 4-methoxybutyl or 4-propoxybutyl.

The N-substituent Y is preferably lower alkyl and, most preferably, methyl.

X as alkyl typically represents the alkyl radicals cited above.

An aryl radical X may be unsubstituted phenyl or naphthyl or phenyl or naphthyl each substituted by halogen, cyano, lower alkyl, $C_5$–$C_6$cycloalkyl, $C_1$–$C_8$acyl, —OR' or —SR'.

X as aryl is preferably a substituted phenyl radical of formula

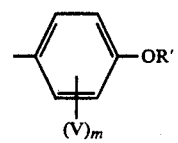

(1a)

wherein R' is alkyl of not more than 12 carbon atoms, unsubstituted or substituted by halogen, hydroxy, cyano or lower alkoxy, or is acyl of 1 to 8 carbon atoms, $C_5$–$C_6$alkyl, phenyl or benzyl. V is hydrogen, halogen, lower alkyl, $C_1$–$C_{12}$alkoxy, $C_1$–$C_8$acyloxy, benzyl, benzyloxy or phenoxy, and m is 1 or 2. One V is preferably in ortho-position to the linkage site.

An acyloxy radical V is typically formyloxy, lower alkanoyloxy such as acetoxy or propionyloxy, or benzoyloxy. V as $C_1$–$C_{12}$alkoxy may be a straight-chain or branched group such as methoxy, ethoxy, isopropoxy, n-butoxy, tert-butoxy, amyloxy, 1,1,3,3-tetramethylbutoxy, n-hexyloxy, n-octyloxy or dodecyloxy.

The substituent X is preferably hydrogen.

Lower alkyl, lower alkoxy and lower alkylthio denote those groups or moieties which contain 1 to 6, preferably 1 to 4, carbon atoms. Illustrative examples of such groups are methyl, ethyl, n-propyl, isopropyl, n-butyl, sec-butyl, amyl, isoamyl or hexyl; methoxy, ethoxy, isopropoxy, isobutoxy, tert-butoxy or amyloxy; and methylthio, ethylthio, propylthio or butylthio.

Halogen is typically fluoro, bromo or, preferably, chloro.

"Acyl" is preferably formyl, lower alkylcarbonyl such as acetyl or propionyl, or benzoyl. Further acyl radicals may be lower alkylsulfonyl such as methylsulfonyl or ethylsulfonyl and also phenylsulfonyl. Benzoyl and phenylsulfonyl may be substituted by halogen, methyl, methoxy or ethoxy.

Particularly important indoline-containing phthalides are those of formula

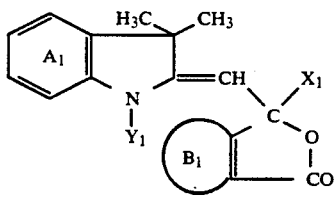

(2)

wherein
the ring $A_1$ is unsubstituted or substituted by halogen, cyano, lower alkyl or lower alkoxy, and the ring $B_1$ is a benzene or pyridine ring which is unsubstituted or substituted by halogen, cyano, lower alkyl, lower alkoxy, lower alkylcarbonylamino or di-lower alkylamino, $Y_1$ is lower alkyl, benzyl or lower alkyl which is substituted by halogen, hydroxy, cyano or lower alkoxy, and $X_1$ is hydrogen or a substituted phenyl radical of formula

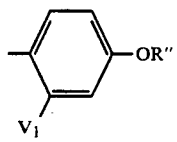

(2a)

wherein R" is lower alkyl or phenyl, and $V_1$ is hydrogen, halogen or lower alkoxy.

Among the phthalides of formula (2), those compounds are preferred in which $X_1$ is hydrogen or a phenyl radical of formula (2a), in which R" is lower alkyl and $V_1$ is hydrogen, and the ring $B_1$ is an unsubstituted or a lower alkoxy-substituted benzene ring. $X_1$ in formula (2) is preferably hydrogen.

Particularly interesting indoline-containing phthalides are those of formula

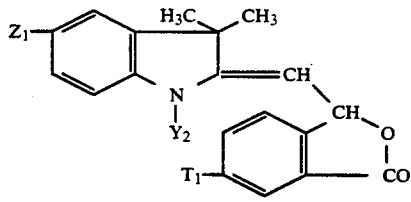

(3)

wherein
$T_1$ is hydrogen or lower alkoxy, preferably methoxy,
$Y_2$ is lower alkyl, preferably methyl, and
$Z_1$ is hydrogen or halogen such as chloro.

The compounds of formula (1) can be prepared by reacting a 2-methylenepyrroline compound of formula

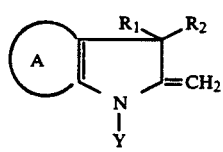

(4)

wherein A, $R_1$, $R_2$ and Y have the given meanings, with an aldehyde acid or ketonic acid of formula

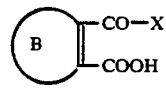

(5)

wherein X and B have the given meanings.

The reaction is conveniently carried out in an organic solvent which is liquid at the reaction temperature, for example in acetonitrile or propionitrile, benzene, xylene, toluene, chlorobenzene or nitrobenzene. The condensation is preferably carried out in the temperature range from 20° to 120° C., most preferably from 40° to 80° C.

Most of the starting materials of formulae (4) and (5) required for the preparation of the phthalides of this invention are known.

Suitable starting materials of formula (4) are:
1,3,3-trimethyl-2-methyleneindoline,
1,3,3-trimethyl-5-chloro-2-methyleneindoline,
1,3,3-trimethyl-2-methylenebenzoindoline,
1,3,3,4,5-pentamethyl-2-methyleneindoline.

Specific examples of starting materials of formula (5) include: phthalaldehyde acid,
5-methoxyphthalaldehyde acid,
5-dimethylaminophthalaldehyde acid,
4'-methoxy-4-dimethylaminobenzophenone-2-carboxylic acid,
4,4'-bis-methoxybenzophenone-2-carboxylic acid,
4-methoxybenzophenone-2-carboxylic acid,
4-dimethylaminobenzophenone-2-carboxylic acid,
4-diethylaminobenzophenone-2-carboxylic acid.

The pyrroline-containing phthalides of formula (1) to (3) are normally colourless or, at most, faintly coloured. When these colour formers are brought into contact with a preferably acid developer, i.e. an electron acceptor, then, depending on the meaning of X and on the developer employed, they develop intense yellow, orange or red images which are fast to sublimation and light.

The phthalides of formulae (1) to (3) are also very useful when combined with one or more other known colour formers, for example 3,3-bis(aminophenyl)phthalides such as CVL, 3-indolyl-3-aminophenylazaphthalides, 3-indolyl-3-aminophenyldiazaphthalides, 3,3-bis(indolyl)phthalides, 3,6-bis(alkoxy)fluorans, 3-aminofluorans, 2,6-diaminofluorans, 2,6-diamino-3-methylfluorans, 3,6-bis(diarylamino)fluorans, leucoauramines, spiropyranes, spirodipyranes, chromenoindoles, chromenopyrazoles, phenoxazines, phenothiazines, quinazolines, rhodamine lactams, carbazolylmethanes or other triarylmethaneleuco dyes, to give blue, navy blue, grey or black images.

The phthalides of formulae (1) to (3) develop on activated clays as well as on phenolic substrates an excellent colour intensity and lightfastness. They are especially suitable for use as rapidly developing colour formers in a heat-sensitive, or especially in a pressure-sensitive, recording material which can also be a copying material. After exposure on a CB sheet, they exhibit a slight decrease in colour strength (CB decline). A pressure-sensitive material comprises, for example, at least one pair of sheets which contain at least one colour former of formulae (1) to (3), dissolved in an organic solvent, and an electron acceptor as developer.

Typical examples of such developers are activated clays such as attapulgite, acid clay, bentonite, montmorillonite, activated clay, for example acid-activated bentonite or montmorillonite, and also zeolith, halloysite, silica, alumina, aluminium sulfate, aluminium phosphate, zinc chloride, zinc nitrate, zirconium dioxide, activated kaolin or any clay. Suitable developers are also acidic organic compounds, for example unsubstituted or ring-substituted phenols, resorcinols, salicylic acids such as 3,5-bis($\alpha,\alpha$-dimethylbenzyl)salicylic acid or 3,5-bis($\alpha$-methylbenzyl)salicylic acid, or salicylates and their metal salts, e.g. zinc salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxymethylene. Mixtures of these monomers and polymers may also be used. Particularly preferred developers are acid-activated bentonite, zinc salicylates or the condensates of p-substituted phenols with formaldehyde. These last mentioned compounds may also be modified with zinc.

The developers may also be used in admixture with other basically inert or almost inert pigments or with other auxiliaries such as silica gel or UV absorbers such as 2-(2-hydroxyphenyl)benzotriazoles. Examples of such pigments are: talcum, titanium dioxide, alumina, hydrated alumina, zinc oxide, chalk, clays such as kaolin, as well as organic pigments, e.g. urea/formaldehyde condensates (BET surface area: 2–75 $m^2/g$) or melamine/formaldehyde condensates.

The colour former effects a coloured marking at those points where it comes into contact with the electron acceptor. To prevent the colour formers contained in the pressure-sensitive recording material from being activated prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet coated with an electron acceptor to produce a coloured image thereon. This colour results from the dye thereby formed and which is absorbed in the visible range of the electromagnetic spectrum.

The colour formers are preferably encapsulated in the form of solutions in organic solvents. Examples of suitable solvents are preferably non-volatile solvents, for example a halogenated paraffin such as chloroparaffin, a halogenated benzene such as trichlorobenzene, or a halogenated diphenyl such as monochlorodiphenyl or trichlorodiphenyl, an ester such as tricresyl phosphate, bis(n-butyl) phthalate, dioctyl phthalate, trichloroethyl phosphate, an aromatic ether such as benzylphenyl ether, a hydrocarbon oil such as paraffin or kerosene, an aromatic hydrocarbon, for example an isopropyl, isobutyl, sec- or tert-butyl derivative of diphenyl, naphthalene or terphenyl; dibenzyl toluene, partially hydrogenated terphenyl, a mono- to tetralkylated diphenylalkane containing 1 to 3 carbon atoms in each of the alkyl moieties; dodecylbenzene, a benzylated xylene, phenylxylyl ethane or other chlorinated or hydrogenated, condensed aromatic hydrocarbons. Mixtures of different solvents, especially mixtures of paraffin oils or kerosene and diisopropylnaphthalene or partially hydrogenated terphenyl, are often used to achieve an optimum solubility for the colour formation, a rapid and intense coloration, and a viscosity which is advantageous for the microencapsulation. When being encapsulated, the phthalides of this invention are soluble and pH stable, for example in the range from 4 to 10.

The capsules walls can be formed evenly around the droplets of the colour former solution by coacervation, and the encapsulating material is described, for example, in U.S. Pat. No. 2,800,457. The capsules may also preferably be formed from an aminoplast or a modified aminoplast by polycondensation, as described in British patent specifications 989 264, 1 156 725, 1 301 052 and 1 355 124. Also suitable are microcapsules which are formed by interfacial polymerisation, for example capsules formed from polyester, polycarbonate, polysulfonamide, polysulfonate, but especially from polyamide or polyurethane.

The microcapsules containing the colour formers of formulae (1) to (3) can be used for the production of a wide range of known kinds of pressure-sensitive copying materials. The various systems differ substantially from one another in the arrangement of the capsules and of the colour reactants, and in the nature of the substrate.

A preferred arrangement is that in which the encapsulated colour former is in the form of a layer on the back of a transfer sheet and the developer is in the form of a layer on the face of a receiver sheet. Another arrangement of the components is that wherein the microcapsules containing the colour former and the developer are in or on the same sheet, in the form of one or more individual layers, or the developer is incorporated in the substrate.

The capsules are preferably secured to the substrate by means of a suitable binder. As paper is the preferred substrate, these binders are principally paper-coating agents, for example gum arabic, polyvinyl alcohol, hydroxymethylcellulose, casein, methyl cellulose, dextrin, starch or starch derivatives or polymer latices. These last mentioned substances are typically butadiene/styrene copolymers or acrylic homopolymers or copolymers.

The paper employed comprises not only normal paper made from cellulose fibres, but also paper in which the cellulose fibres are replaced (partially or completely) by synthetic polymers. The substrate may also be a plastic sheet.

The copying material preferably comprises a capsule-free layer which contains the colour former and a colour developing layer containing, as colour developer, at least one inorganic metal salt of a polyvalent metal, preferably a halide or a nitrate, for example zinc chloride, zinc nitrate or a mixture thereof.

The compounds of formulae (1) to (3) may also be used as colour formers in a thermoreactive recording material. This recording material usually comprises at least one substrate, one colour former, one electron acceptor and, in some cases, also a binder and/or wax. If desired, the recording material may also contain activators or sensitisers.

Thermoreactive recording systems comprise, for example, heat-sensitive recording or copying materials and papers. These systems are used, for example, for recording information, for example in electronic computers, teleprinters or telewriters, or in recording and measuring instruments, such as electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. An alternative method comprises dispersing both the colour former and the developer in one layer. By means of heat the layer or layers are softened at specific areas, whereupon the desired colour develops at once at the heated areas.

Suitable developers are the same electron acceptors as are used in pressure-sensitive papers. Examples of developers are the previously mentioned clays and phenolic resins, or also the phenolic compounds described, for example, in German Offenlegungsschrift 1 251 348, for example 4-tert-butylphenol, 4-phenylphenol, methylene-bis(p-phenylphenol), 4-hydroxydiphenyl ether, α-naphthol, β-naphthol, methyl 4-hydroxybenzoate or benzyl 4-hydroxybenzoate, 4-hydroxydiphenylsulfone, 4'-hydroxy-4-methyldiphenylsulfone, 4'-hydroxy-4-isopropoxydiphenylsulfone, 4-hydroxyacetophenone, 2,2'-dihydroxydiphenyl, 4,4'-cyclohexylidenediphenol, 4,4'-isopropylidenediphenol, 4,4'-isopropylidene-bis(2-methylphenol), an antipyrine complex of zinc thiocyanate, a pyridine complex of zinc thiocyanate, 4,4'-bis(4-hydroxyphenyl)valeric acid, hydroquinone, pyrogallol, phloroglucinol, p-, m-and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the preparation of the thermoreactive recording material. These binders are normally water-soluble, whereas the phthalides and the developer are sparingly soluble or insoluble in water. The binder should be able to disperse and fix the colour former and the developer at room temperature.

When heat is applied, the binder softens or melts, so that the colour former comes in contact with the developer and a colour is able to form. Examples of binders which are soluble, or at least swellable, in water are hydrophilic polymers such as polyvinyl alcohol, polyacrylic acid, hydroxyethylcellulose, methyl cellulose, carboxymethylcellulose, polyacrylamide, polyvinyl pyrrolidone, gelatin, starch or etherified corn starch.

If the colour former and the developer are present in two separate layers, it is possible to use water-insoluble binders, i.e., binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

To ensure the stability of the heat-sensitive recording material or the density of the developed image, the material may be provided with an additional protective layer. Such protective layers consist as a rule of water-soluble and/or water-insoluble resins which are customary polymer materials or aqueous emulsions thereof.

The thermoreactive coatings may contain further modifiers. To improve the degree of whiteness, to facilitate the printing of papers, and to prevent the heated pen from sticking, the coatings may contain, for example, talcum, titanium dioxide, zinc oxide, aluminium hydroxide, calcium carbonate (e.g., chalk), clays or also organic pigments, for example urea/formaldehyde polymers. In order to effect the colour formation only within a limited temperature range, it is possible to add substances such as urea, thiourea, diphenyl thiourea, acetamide, acetanilide, bis(stearoyl)ethylenediamide, benzosulfanilide, stearamide, phthalic anhydride, metal stearates such as zinc stearate, phthalonitrile, dimethyl terephthalate, dibenzyl terephthalate or other suitable fusible products which induce the simultaneous melting of the colour former and the developer. Thermographic recording materials preferably contain waxes such as carnauba wax, montan wax, paraffin wax, polyethylene wax, condensates of higher fatty acid amides and formaldehyde, or condensates of higher fatty acids and ethylenediamine.

A further utility of the compounds of formulae (1) to (3) is the production of a coloured image with the photocurable microcapsules described in German Offenlegungsschrift 3 247 488.

In the following Examples parts and percentages are by weight, unless otherwise stated.

EXAMPLE 1

1.8 g of 5-methoxyphthalaldehyde acid and 1.93 g of 1,3,3-trimethyl-2-methyleneindoline (Fischer base) are stirred in 15 ml of toluene for 1 hour at 50° C. The reaction mixture is concentrated and chromatographed on silica gel, giving 3.24 g of a compound of formula

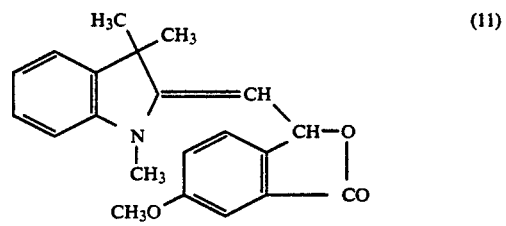

(11)

with a melting point of 75°–85° C. This compound produces a lightfast yellow image on paper coated with activated clay ($\lambda_{max}=440$ nm).

EXAMPLE 2

1.53 g of phthalaldehyde acid and 2.23 g of 1,3,3-trimethyl-2-methylene-5-chloroindoline are stirred in 20 ml of toluene for 30 minutes at 50° C. The product crystallises from the cooled reaction mixture and is isolated by filtration and dried, giving 1.0 g of a compound of formula

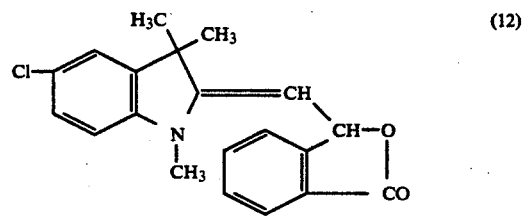

(12)

with a melting point of 191°–192° C. This compound produces a yellow image on paper coated with activated clay.

EXAMPLE 3

Preparation of a pressure-sensitive copying paper

A solution of 3 g of the phthalide of formula (11) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with activated clay as colour developer. The first sheet containing the colour former and the sheet coated with the developer are laid on top of each other with the coated sides face to face. Pressure is exerted on the first sheet by writing by hand or typewriter and an intense yellow copy of excellent lightfastnes develops immediately on the sheet coated with the developer.

EXAMPLE 4

1 g of the phthalide of formula (12) according to Example 2 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by writing by hand or typewriter and an intense lightfast yellow copy develops immediately on the sheet coated with the colour former.

EXAMPLE 5

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of ca. 5 μm. In a second ball mill, 6 g of the phthalide of formula (11) obtained in Example 1, 3 g of a 88% hydrolysed polyvinyl alcohol and 60 ml of water are ground to a particle size of ca. 3 μm.

Both dispersions are mixed and applied to paper to a dry coating weight of 5.5 g/m². An intense yellow image of excellent fastness to light and sublimation is produced by contacting the paper with a heated stylus.

EXAMPLE 6

1.1 g of the colour former according to EP-A-90 810 714.7 of formula

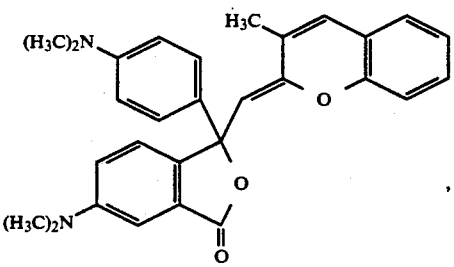

2.3 g of 3,3-bis(1'-n-octyl-2'-methylindol-3'-yl)phthalide and 0.6 g of the colour former of Example 1 are dissolved at 70°-80° C. in 100 g of partially hydrogenated terphenyl. The cooled solution is applied with a photogravure machine to a presized paper which is coated with activated clay. An intense and lightfast black image develops immediately.

What is claimed is:

1. A phthalide of formula

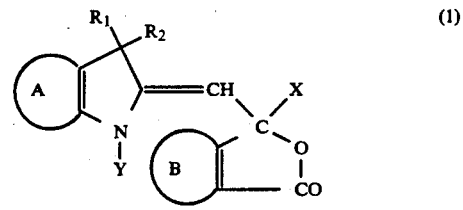

wherein $R_1$ and $R_2$ are each independently of the other lower alkyl, $C_5$-$C_7$cycloalkyl or benzyl or, when taken together, are $C_4$-$C_6$alkylene, Y is alkyl of not more than 12 carbon atoms, unsubstituted or substituted by halogen, cyano, hydroxy or lower alkoxy, or is benzyl, X is hydrogen, alkyl of 1 to 12 carbon atoms or unsubstituted phenyl or naphthyl or phenyl or naphthyl each substituted by halogen, cyano, lower alkyl, $C_5$-$C_6$cycloalkyl, $C_1$-$C_8$acyl, —OR' or —SR', wherein R' is alkyl of not more than 12 carbon atoms, unsubstituted or substituted by halogen, hydroxy, cyano or lower alkoxy, or is acyl of 1 to 8 carbon atoms, $C_5$-$C_6$alkyl, phenyl or benzyl, and the ring A is a benzene or naphthalene ring which is unsubstituted or substituted by one or more members selected from the group consisting of halogen; cyano, lower alkyl, lower alkoxy or lower alkoxycarbonyl, and the ring B is a benzene or naphthalene ring which is unsubstituted or substituted by halogen, cyano, nitro, lower alkyl, lower alkoxy, lower alkylthio, lower alkylcarbonyl, lower alkoxycarbonyl, amino, lower alkylamino, di-lower alkylamino or lower alkylcarbonylamino.

2. A phthalide of formula (1) according to claim 1, wherein Y is lower alkyl.

3. A phthalide of formula (1) according to claim 1, wherein X is hydrogen.

4. A phthalide of formula (1) according to claim 1, wherein the ring A is a benzene ring which is unsubstituted or substituted by halogen or lower alkyl.

5. A phthalide of formula (1) according to claim 1, wherein the ring B is a benzene ring which is unsubstituted or substituted by chloro, lower alkoxy or di-lower alkylamino.

6. A phthalide according to claim 1, of formula

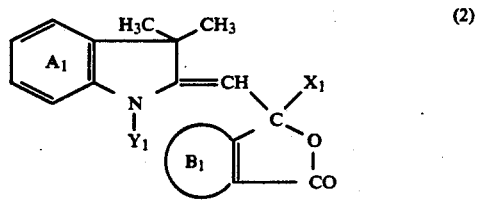

wherein the ring $A_1$ is unsubstituted or substituted by halogen, cyano, lower alkyl or lower alkoxy, and the ring $B_1$ is a benzene ring which is unsubstituted or substituted by halogen, cyano, lower alkyl, lower alkoxy, lower alkylcarbonylamino or di-lower alkylamino, $Y_1$ is lower alkyl, benzyl or lower alkyl which is substituted by halogen, hydroxy, cyano, lower alkoxy, and $X_1$ is hydrogen or a substituted phenyl radical of formula

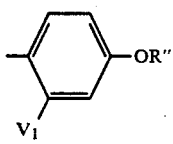
(2a)

wherein R" is lower alkyl or phenyl, and $V_1$ is hydrogen, halogen or lower alkoxy.

7. A phthalide of formula (2) according to claim 6, wherein $X_1$ is hydrogen or a phenyl radical of formula (2a), wherein R" is lower alkyl and $V_1$ is hydrogen, and the ring $B_1$ is an unsubstituted or a lower alkoxy-substituted benzene ring.

8. A phthalide according to claim 1, of formula

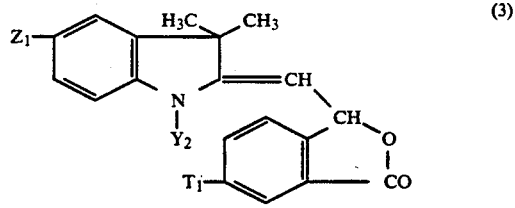
(3)

wherein
$T_1$ is hydrogen or lower alkoxy,
$Y_2$ is lower alkyl, and
$Z_1$ is hydrogen or halogen.

9. A phthalide of formula (1) according to claim 1, wherein the ring B is an unsubstituted benzene ring or a benzene ring substituted as defined in claim 1.

* * * * *